United States Patent [19]

Stiffey

[11] Patent Number: 4,950,594
[45] Date of Patent: Aug. 21, 1990

[54] MICROBIOLOGICAL ASSAY USING BIOLUMINESCENT ORGANISM

[75] Inventor: Arthur V. Stiffey, Slidell, La.

[73] Assignee: The United States of America as represented by the Secretary of the Navy, Washington, D.C.

[21] Appl. No.: 135,969

[22] Filed: Dec. 21, 1987

[51] Int. Cl.$^5$ .......................... C12Q 1/18; C12Q 1/02; C12R 1/90
[52] U.S. Cl. ........................................ 435/32; 435/29; 435/251; 435/258; 435/947; 436/30
[58] Field of Search .................. 435/29, 32, 244, 251, 435/258, 947; 436/30

[56] References Cited

U.S. PATENT DOCUMENTS 4,513,280  4/1985  Hannan et al. .................... 340/632
4,689,305  8/1987  Stiffey et al. ....................... 435/291

OTHER PUBLICATIONS

Nealson, K. H., ed., Bioluminescence Current Perspectives, Burgess Publishing Co., Minneapolis, MN, pp. 95–106, 1981.
Bold, H. C. et al., "Division Pyrrhophytophyta", in Introduction to the Algae, (1978), Prentice-Hall, Inc., New Jersey, pp. 417–450.
50 Federal Register 34591-01, Appendix 3, "Drilling Fluids Toxicity Test", pp. 34631–34633 (1985).
Guillard and Ryther, "Studies of Marine Planktonic Diatoms", Can. Jour of Microbiol. 8, 229–239 (1962).
Anderson, Kulis and Binder, "Sexuality and Cyst Formation in the Dinoflagellate Gonyaulax Tamaronsis: Cyst Yield in Batch Cultures", J. Phycol. 20, 418–425 (1984).
Lyman and Fleming, "Composition of Sea Water", Jour. of Marine Research, vol. III-2, 134–146 (1940).
Hannan, Stiffey and Jarvis, "Bioluminescence as the Basis for the Detection of Trichothecenes", NRL Memorandum Report 5738 (Mar., 1986).
Microbics Corp. Publication 55J003, "Microtox Bibliography", 1–6 (1988).
Strosher, "A Comparison of Biological Testing Methods in Association with Chemical Analyses to Evaluate Toxicity of Waste Drilling Fluids in Alberta", vol. I, Canadian Petroleum Association.
Bulich, "Bioluminescence Assays", Chapter 4, 57–74, in Bitton and Dutka (eds.), Toxicity Testing Using Micro Organisms, vol. 1, CRC Press (1986).

Primary Examiner—Esther L. Kepplinger
Assistant Examiner—Toni R. Scheiner
Attorney, Agent, or Firm—Thomas M. Phillips; Thomas E. McDonald

[57] ABSTRACT

A microbiological assay based on bioluminesce employing the bioluminescent dinoflagellate Pyrocystis lunula. An oil well drilling fluid sample is prepared according to E. P. A. procedures to obtain a suspended particulate phase sample. An aliquot of the sample is added to a growth medium containing Pyrocystis lunula in suspension. The mixture is agitated to subject the Pyrocystis lunula to a shear stress. Light emitted as a result of the shear stress on the Pyrocystis lunula is measure and compared with a control to determine if there is diminution of light produced by the Pyrocystis lunula in the mixture. Diminution of light production is an indication of the presence of a toxic substance in the sample.

13 Claims, No Drawings

MICROBIOLOGICAL ASSAY USING BIOLUMINESCENT ORGANISM

BACKGROUND OF THE INVENTION

1. Field of the Invention

The present invention relates to testing processes for toxicity involving microorganisms and more particularly to testing processes for toxicity involving bioluminescent organisms.

2. Description of the Prior Art

The present known method of testing oil well drilling fluids for toxicity is prescribed by the Environmental Protection Agency (E. P. A.) as published in 50 Federal Register 34592-01, Appendix 3. This method employs the mysid shrimp (*Mysidopsis bahia*) as the assay organism. Equal sized groups of shrimp are placed in holding containers. One group, the control, receives no treatment while the other containers receive dilutions of the test samples of oil well drilling fluids. After 96 hours, dead and living shrimp are counted and the median lethal concentration, LC-50, calculated as that concentration of drilling fluid that results in the mortality of 50 percent of the test organisms. The shrimp are difficult to raise and handle as laboratory assay organisms. This method is labor intensive, because it requires a long assay time (about 96 hours) and because the mysid shrimp are extremely sensitive to changes in laboratory conditions, the process sometimes requires repeated assays and has a coefficient of variation of 20 to 40 percent.

SUMMARY OF THE INVENTION

A microbiological assay in which the assay organism is the dinoflagellate, *Pyrocystis lunula*. A sample of a substance to be assayed is added to known numbers of the bioluminescent dinoflagellate and the mixture is agitated to subject the organisms to a shear stress causing them to emit light. The amount of light emitted is measured and compared with the amount of light emitted by a known non-toxic control mixture to determine if there is diminution or non-diminution of light emitted by the sample under test which is an indication of the presence or absence of toxicity, respectively.

Accordingly, an object of the present invention is the provision of an improved method of testing substances for toxicity.

A further object of the invention is the provision of an improved method of testing oil well drilling fluids for toxicity using bioluminescent dinoflagellate (*Pyrocystis lunula*).

Other objects, advantages and novel features of the invention will become apparent from the following detailed description.

DESCRIPTION OF THE PREFERRED EMBODIMENT

Dinoflagellate (*Pyrocystis lunula*) is used as the assay organism. It contains many cysts which emit light when the organism is subjected to a shear stress, such as in stirring. It has a slow rate of growth (doubling time is approximately 4 days). Transfers need only be done monthly. The organisms require no special handling and benefit from very static conditions. Stock cultures contain approximately 2000 cells/ml. *Pyrocystis lunula* is maintained in culture on f/2 medium (one-half strength medium f) described by Gaillard and Ryther, "Studies of Marine Planktonic Diatoms", Can. Jour. Microbiol. 8, 229, 1962. This medium was modified by the omission of silicate and the addition of TRIS buffer to increase the final ph to 7.6. Artificial sea water is the base for this medium and is prepared with C. P. salts and distilled water from the formula of Lyman and Fleming, "Composition of Sea Water", J. Mar. Res. 3, 134, 1940. Temperature of incubation was 20° ±1° C. Illumination was provided by cool white fluorescent lamps, shaded to obtain a light intensity of 17 micro einsteins/cm$^2$. Illumination was on a cycle of 12 hours light and 12 hours dark. Cells are counted with the aid of a Sedwick Rafter chamber and their concentration adjusted to 100 cells per ml.

To assemble the assay, three ml aliquots of the cell suspension at 100 cells/ml are dispensed into glass vials, 22×50 mm. Samples of oil well drilling fluids are adjusted to pH 7.6, diluted 1-9 and added in 10 microliter and 20 microliter amounts to the glass vials containing the test cultures. Control suspensions contained no additives. The vials containing the test cultures were placed in a carousel and kept motionless in the dark for 4½ hours prior to the assay.

To be certain that the dinoflagellate culture emits the maximum amount of light, it is necessary that the culture be stirred vigorously. Stirring is accomplished with an acrylic rod equipped on one end with a thin strip of acrylic plastic. The other end of the rod is fitted into the chuck of a variable speed electric motor drive set at about 100 rpm. The rod in then inserted approximately ⅔ of the way into the sample vial. Stirring should be continued for about 2 minutes.

Bioluminescence is measured with the solid state photometer described in U.S. Pat. No. 4,689,305 to Stiffey, et al. A multi-range stripchart recorder with a chart speed of 5 cm/minute may be connected to the photometer. If this is done, the photometer should be adjusted such that the recorder registers the cumulative light fluxes as a function of time.

Percentage of bioluminescent quenching is calculated with the equation:

$$\% \text{ quenching} = \frac{C - E}{C} \times 100$$

where C=displacement of the recorder pen, in mm, during stirring of the non-toxic control culture, and E=the displacement of the pen during stirring of the test suspension. Total elapsed time of assay is approximately 2½ hours.

In practicing the invention, samples were assayed as subsamples of samples previously assayed using the mysid shrimp test. On receipt of samples they were stored at 4° C. until assayed. The samples were assayed as described above and the following results are shown in Table I.

TABLE I

| SAMPLE NUMBER | BIOLUMINESCENT INHIBITION | | BIOLUMINESCENCE Toxic = + Nontoxic = − | SHRIMP ASSAY Toxic = + Nontoxic = − |
| --- | --- | --- | --- | --- |
| | DILUTION 3% | DILUTION 6% | | |
| OCS6 7750 * | — | — | — | — |
| GC2M7 ** | 19.7% | 20.7% | + | + |

TABLE I-continued

| SAMPLE NUMBER | BIOLUMINESCENT INHIBITION | | BIOLUMINESCENCE Toxic = + Nontoxic = − | SHRIMP ASSAY Toxic = + Nontoxic = − |
| --- | --- | --- | --- | --- |
| | DILUTION 3% | DILUTION 6% | | |
| 40 *** | — | — | — | — |
| 45 *** | — | 18.6% | + | + |
| 0448701 *** | 14.0% | 21.2% | + | + |
| 0428702 *** | 17.3% | 28.3% | + | + |
| 48 *** | — | — | — | — |
| 41 *** | — | — | — | — |
| 0118702 ** | — | — | — | — |
| 0258702 *** | 21.8% | 36.9% | + | + |
| 0228701 *** | 33.0% | 36.0% | + | + |
| 1360 * | — | — | — | — |
| 1366 * | — | — | — | — |

\* = COMMERCIAL FLUID
\*\* = EXPERIMENTAL SAMPLE
\*\*\* = FIELD SAMPLE

Three varieties of samples were assayed: (1) Commercial fluids obtained from local suppliers to drilling rigs; (2) Experimental drilling fluids obtained from commercial oil companies and (3) Field samples obtained from sources using the mysid shrimp process outlined above.

Negative values of the bioluminescence results indicate that test samples did not significantly inhibit light production from the controls at the 1% confidence level. Confidence levels were calculated by the Wilcoxon's Rank Sum test, testing differences in variability in unpaired replicates.

In all cases where bioluminescence values were positive, light production was significantly inhibited from the controls at the 1% confidence level at 3% and 6% dilution of the sample. Sample No. 45 was positive at the 5% confidence level. Assay precision for the bioluminescence assay was calculated as coefficient of variation and was 10% or less for the samples assayed of Table I.

Samples of the unused drilling fluid analyzed using the present invention were also analyzed using the mysid shrimp assay with concurring results.

Obviously many modifications and variations of the present invention are possible in light of the above teachings. It is therefore to be understood that within the scope of the appended claims the invention may be practiced otherwise than as specifically described.

What is claimed:

1. A method of assaying drilling fluids for toxicity, comprising the steps of:
    (a) preparing a drilling fluid sample to obtain a suspended particulate phase sample,
    (b) preparing a non-toxic control containing *Pyrocystis lunula* in suspension,
    (c) removing aliquots from said suspended particulate phase sample,
    (d) placing said aliquots in a growth medium containing *Pyrocystis lunula* in suspension to provide a mixture of said aliquots and said *Pyrocystis lunula*, said mixture being contained within a test vial of light-transmitting material,
    (e) imparting rotary motion to said mixture to subject said suspended *Pyrocystis lunula* of said mixture to a shear stress for a predetermined time,
    (f) simultaneously with step (e), detecting the light production of said mixture for said predetermined time,
    (g) subjecting said suspended *Pyrocystis lunula* of said non-toxic control to a shear stress for said predetermined time,
    (h) simultaneously with step (g), detecting the light production of said non-toxic control for said predetermined time, and
    (i) comparing the light production of said mixture with the light production of said non-toxic control to determine diminution of light production which is an indication of the presence of a toxic substance in said sample.

2. A method of assaying drilling fluids for toxicity, comprising the steps of:
    (a) preparing a drilling fluid sample to obtain a suspended particulate phase sample,
    (b) preparing a non-toxic control containing *Pyrocystis lunula* in suspension,
    (c) removing aliquots from said suspended particulate phase sample,
    (d) placing said aliquots in a growth medium containing *Pyrocystis lunula* in suspension to provide a mixture of said aliquots and said *Pyrocystis lunula*,
    (e) stirring said mixture for a predetermined time to ensure emission of a maximum amount of light by said mixture,
    (f) detecting the light production of said mixture during the predetermined time that the mixture is being stirred,
    (g) stirring the non-toxic control for said predetermined time to ensure emission of a maximum amount of light by the non-toxic control,
    (h) detecting the light production of the non-toxic control during the predetermined time that the non-toxic control is being stirred, and
    (i) comparing said light production of said mixture with said light production of said non-toxic control to determine diminution of light production which is an indication of the presence of a toxic substance in said sample.

3. A method of assaying drilling fluids for toxicity, comprising the steps of:
    (a) preparing a drilling fluid sample to obtain a suspended particulate phase sample,
    (b) preparing a non-toxic control containing *Pyrocystis lunula* in suspension,
    (c) removing aliquots from said suspended particulate phase sample,
    (d) placing said aliquots in 3 ml of growth medium containing 300 *Pyrocystis lunula* cells to provide a mixture of said aliquots and said *Pyrocystis lunula*, (e) agitating said mixture for a predetermined time sufficient for the emission of a maximum amount of light by said mixture, (f) detecting the cumulative light flux of said mixture during said agitation of said mixture, (g) agitating said non-toxic control for said predetermined time, (h) detecting the cumulative light flux of said non-toxic control during said agitation of said non-toxic control, and (i) comparing said cumulative light flux of said mixture with said cumulative light flux of said non-toxic control to determine diminution of light production which is an indication of the presence of a toxic substance in said sample.

4. A method of assaying drilling fluids for toxicity, comprising the steps of:

(a) preparing a drilling fluid sample to obtain a suspended particulate phase sample, (b) preparing a non-toxic control containing *Pyrocystis lunula* in suspension, (c) removing a 10 μl aliquot from said suspended particulate phase sample, (d) placing said aliquot in 3 ml of growth medium containing 300 Pyrocystis lunula cells to provide a mixture of said aliquots and said *Pyrocystis lunula,*

(e) agitating said mixture for a predetermined time, (f) detecting the light production of said mixture during the agitation of the mixture, (g) agitating said non-toxic control for said predetermined time, (h) detecting the light production of said non-toxic control during the agitation of the non-toxic control, and (i) comparing said light production of said mixture with said light production of said non-toxic control to determine diminution of light production which is an indication the presence of a toxic substance in said sample.

5. A method of assaying drilling fluids for toxicity, comprising the steps of:

(a) preparing a drilling fluid sample to obtain a suspended particulate phase sample, (b) preparing a non-toxic control containing bioluminescent dinoflagellates of the genus Pyrocystis in suspension, (c) removing aliquots from said suspended particulate phase sample, (d) placing said aliquots in a predetermined amount of growth medium containing a predetermined number of bioluminescent dinoflagellate cells of the genus Pyrocystis in suspension to provide a mixture of said aliquots and said dinoflagellate cells in suspension, (e) agitating said mixture for a predetermined time, (f) detecting the light production of said mixture during said mixture agitation, (g) agitating said non-toxic control for said predetermined time, (h) detecting the light production of said non-toxic control during the agitation of the non-toxic control, and (i) comparing said light production of said mixture with said light production of said non-toxic control to determine diminution of light production which is an indication of the presence of a toxic substance in said sample.

6. A method of assaying drilling fluids for toxicity, comprising the steps of:

preparing an assay medium containing a predetermined number per unit volume of bioluminescent dinoflagellate cells of the genus Pyrocystis in suspension;

removing a plurality of aliquots from the assay medium, including a first aliquot designated as a non-toxic control and a second aliquot;

processing a drilling fluid sample to obtain a suspended particulate phase (SPP) of the sample;

adding a predetermined quantity of the SPP to the second aliquot to obtain a mixture of the SPP and the dinoflagellate cells in suspension;

agitating said mixture for a predetermined agitation time;

detecting light production of said mixture during the agitation of the mixture;

agitating the non-toxic control for said predetermined agitation time;

detecting light production of said non-toxic control during the agitation of the non-toxic control; and comparing the light production of said mixture with the light production of the non-toxic control to determine diminution of light production which is an indication of the presence of a toxic substance in the sample.

7. A method of assaying drilling fluids for toxicity, as described in claim 6, wherein the step of processing a drilling fluid sample to obtain a suspended particulate phase (SPP) comprises the steps of:

mixing the drilling fluid sample with filtered test seawater to produce a slurry having a predetermined volumetric ratio of drilling fluid to seawater;

allowing the slurry to settle in a container for a sufficient settling time for any solid phase to settle to the bottom of the container; and decanting the suspended particulate phase (SPP) into an appropriate container.

8. A method of assaying drilling fluids for toxicity, as described in claim 7, wherein the step of processing a drilling fluid sample to obtain a suspended particulate phase (SPP) further comprises the steps of:

measuring the pH of the slurry; and adjusting the pH of the slurry to be approximately the same as the pH of the test seawater.

9. A method of assaying drilling fluids for toxicity, as described in claim 6, wherein said luminescent dinoflagellate cells are *Pyrocystis lunula* cells.

10. A method of assaying drilling fluids for toxicity, as described in claim 6, wherein the predetermined agitation time of said mixture and the non-toxic control is of sufficient length to ensure emission of a maximum amount of light by both the mixture and the non-toxic control.

11. A method of assaying drilling fluids for toxicity, as described in claim 10, wherein the detected light productions of the mixture and the non-toxic control are cumulative light productions.

12. A method of assaying drilling fluids for toxicity, as described in claim 6, wherein the mixture and the non-toxic control are disposed in identical glass vials, and agitation of the mixture and the non-toxic control is achieved by stirring the mixture and the non-toxic control with respective rotating stirrer elements inserted into the glass vials.

13. A method of assaying drilling fluids for toxicity, as described in claim 6, wherein:

during the step of agitating said mixture, the mixture is disposed within a test vial of light-transmitting material, and agitation of the mixture is achieved by imparting rotary motion to the mixture; and during the step of agitating said non-toxic control, the non-toxic control is disposed within a test vial of light-transmitting material, and agitation of the non-toxic control is achieved by imparting rotary motion to the mixture.

* * * * *